US011208626B2

United States Patent
Mason et al.

(10) Patent No.: US 11,208,626 B2
(45) Date of Patent: Dec. 28, 2021

(54) CELL CULTURE DEVICE, SYSTEM AND METHODS OF USE THEREOF

(71) Applicant: Ori Biotech Ltd., London (GB)

(72) Inventors: Christopher Mason, Cambridge, MA (US); Farlan Veraitch, London (GB)

(73) Assignee: Ori Biotech Ltd., London (GB)

( * ) Notice: Subject to any disclaimer, the term of this patent is extended or adjusted under 35 U.S.C. 154(b) by 418 days.

(21) Appl. No.: 15/575,105

(22) PCT Filed: May 20, 2016

(86) PCT No.: PCT/GB2016/051451
§ 371 (c)(1),
(2) Date: Nov. 17, 2017

(87) PCT Pub. No.: WO2016/185221
PCT Pub. Date: Nov. 24, 2016

(65) Prior Publication Data
US 2018/0142200 A1 May 24, 2018

(30) Foreign Application Priority Data

May 21, 2015 (GB) ...................... 1508752

(51) Int. Cl.
*C12M 1/34* (2006.01)
*A61M 5/28* (2006.01)
(Continued)

(52) U.S. Cl.
CPC ............ *C12M 41/44* (2013.01); *A61M 5/148* (2013.01); *A61M 5/282* (2013.01); *C12M 23/26* (2013.01); *C12M 41/32* (2013.01)

(58) Field of Classification Search
CPC ...... C12M 41/44; C12M 23/26; C12M 41/32; A61M 5/148; A61M 5/282
See application file for complete search history.

(56) References Cited

U.S. PATENT DOCUMENTS

| 3,712,295 A | 1/1973 | Kline |
| 2003/0143727 A1* | 7/2003 | Chang ................... C12M 23/34 435/289.1 |

(Continued)

FOREIGN PATENT DOCUMENTS

| EP | 1 679 365 A1 | 7/2006 |
| GB | 1 232 407 A | 5/1971 |

(Continued)

*Primary Examiner* — William H. Beisner
*Assistant Examiner* — Danielle B Henkel
(74) *Attorney, Agent, or Firm* — Blank Rome LLP

(57) ABSTRACT

The present invention provides a method for culturing cells in a cell culture container having a base section, a top section arranged in parallel with the top section and a wall element arranged between the top section and the base section and defining an internal lumen of the container, in which the wall element of the container is compressible with respect to the top and bottom section, and in which the top section of the container has an optionally sealable inlet, in which the container is composed of a flexible material, comprising culturing cells in a culture medium in the cell culture container. Also provide is a cell culture container having a base section, a top section arranged in parallel with the top section and a wall element arranged between the top section and the base section and defining an internal lumen of the container, in which the wall element of the container is compressible with respect to the top and bottom section, and in which the top section of the container has an optionally sealable inlet, in which the wall element of the container is composed of a flexible material.

15 Claims, 16 Drawing Sheets

(51) Int. Cl.
  *C12M 1/00* (2006.01)
  *A61M 5/148* (2006.01)

(56) References Cited

U.S. PATENT DOCUMENTS

| | | | |
|---|---|---|---|
| 2003/0157709 A1* | 8/2003 | DiMilla | C12M 29/10 |
| | | | 435/325 |
| 2007/0224676 A1 | 9/2007 | Haq | |
| 2007/0254356 A1 | 11/2007 | Wilson et al. | |
| 2011/0070648 A1* | 3/2011 | Anneren | C12M 25/16 |
| | | | 435/380 |
| 2013/0281940 A1 | 10/2013 | Gelblum et al. | |

FOREIGN PATENT DOCUMENTS

| | | | |
|---|---|---|---|
| JP | 2013-74889 A | 4/2013 | |
| WO | WO1992/11355 A1 * | 7/1992 | C12N 5/02 |
| WO | WO 2005/037984 A1 | 4/2005 | |
| WO | WO 2008/088371 A2 | 7/2008 | |
| WO | WO 2013/021079 A1 | 2/2013 | |

* cited by examiner

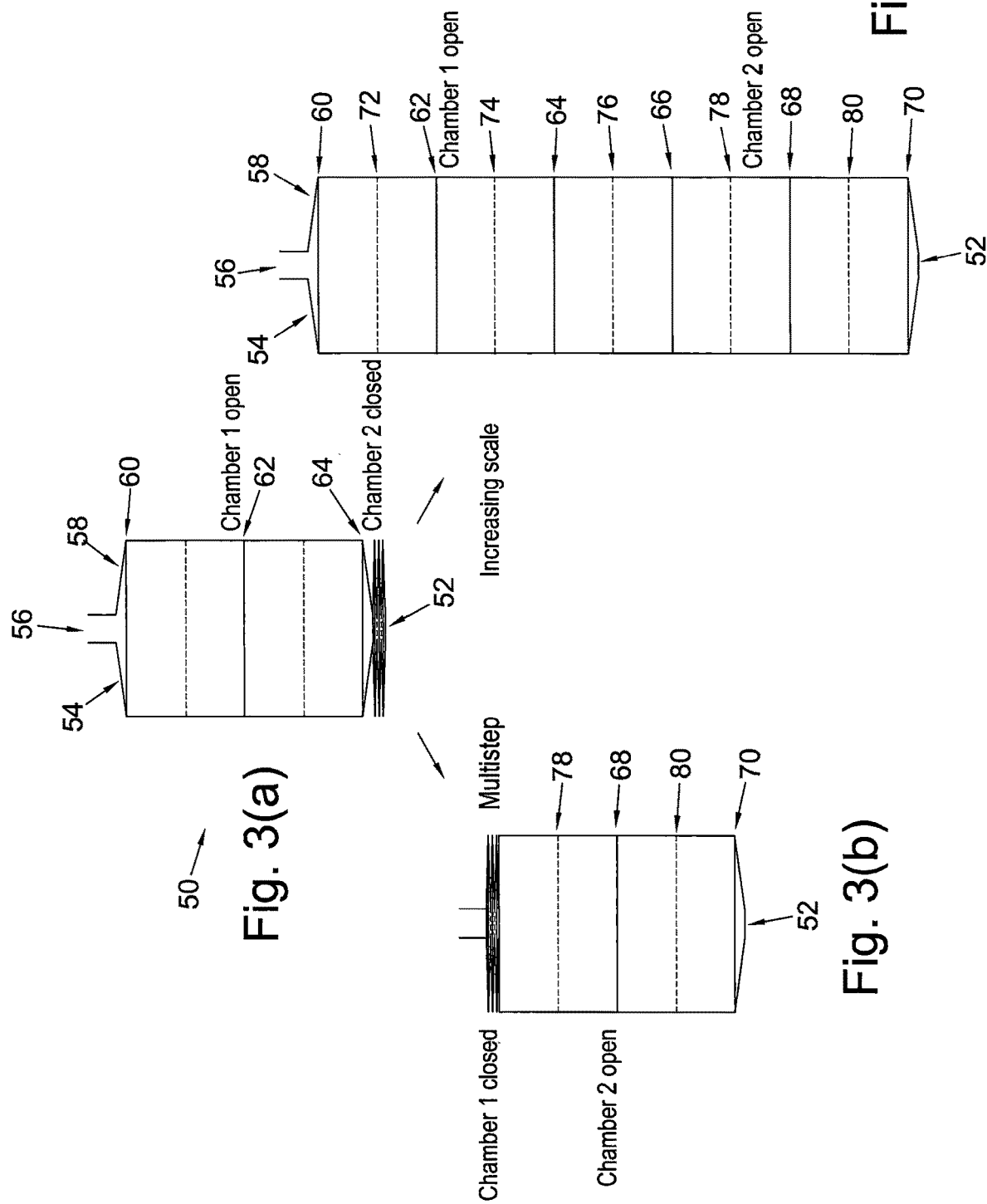

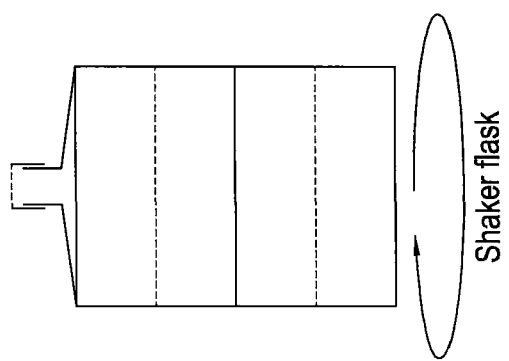
Fig. 6(a) Shaker flask
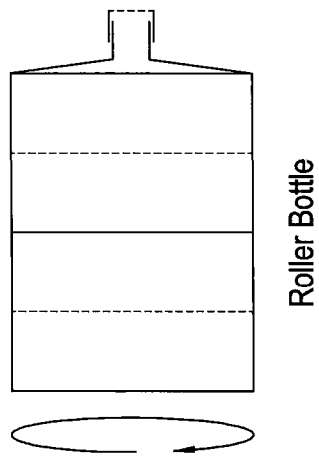
Fig. 6(b) Roller Bottle
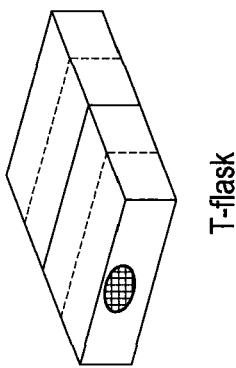
Fig. 6(c) T-flask

ALTERNATIVE CONFIGURATIONS

SIDE VIEWS

Rigid wires

Flexible material engineered to fold in specific location

Flexible construction with a wire frame

The screwed concertina

TOP VIEWS

Different shapes

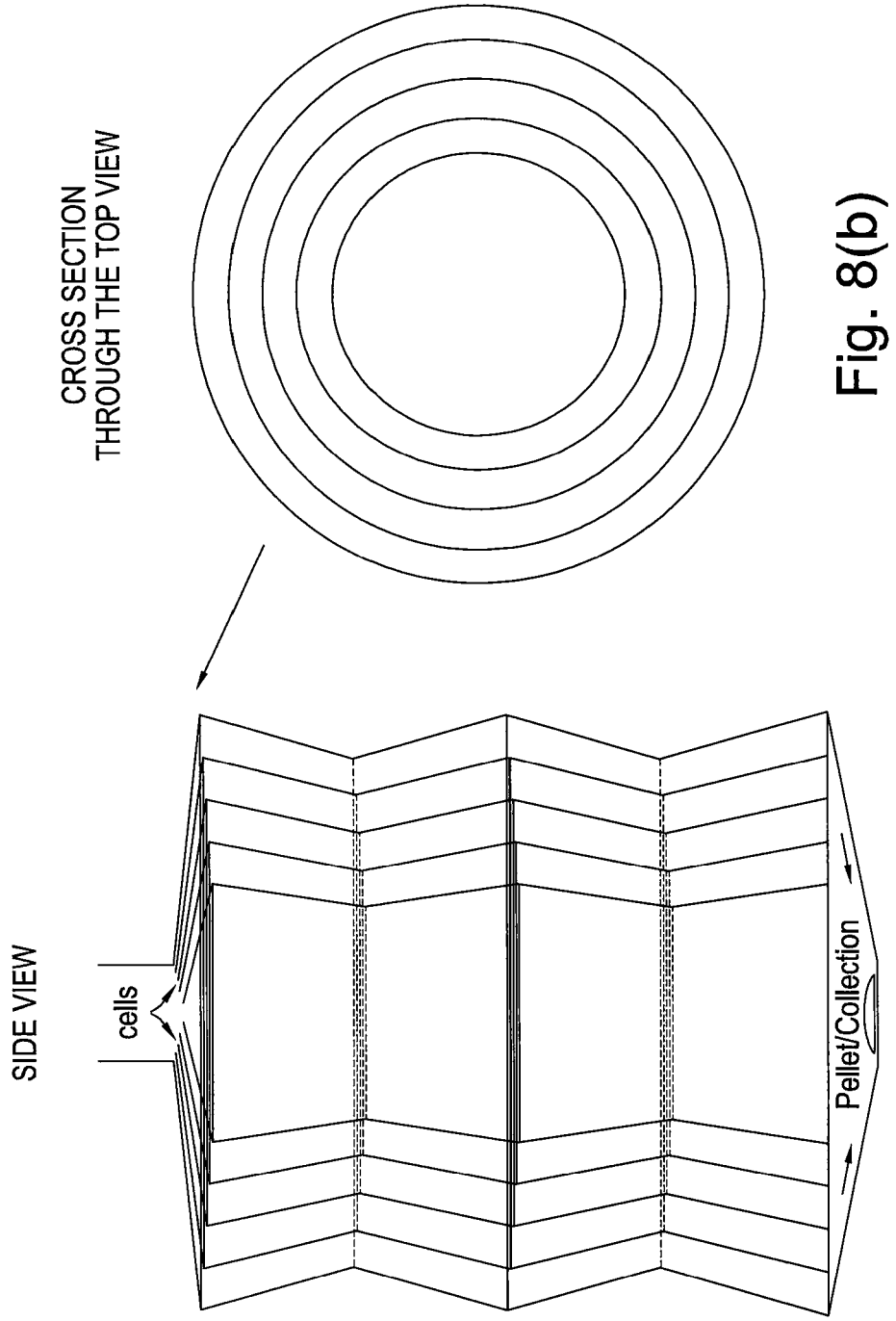

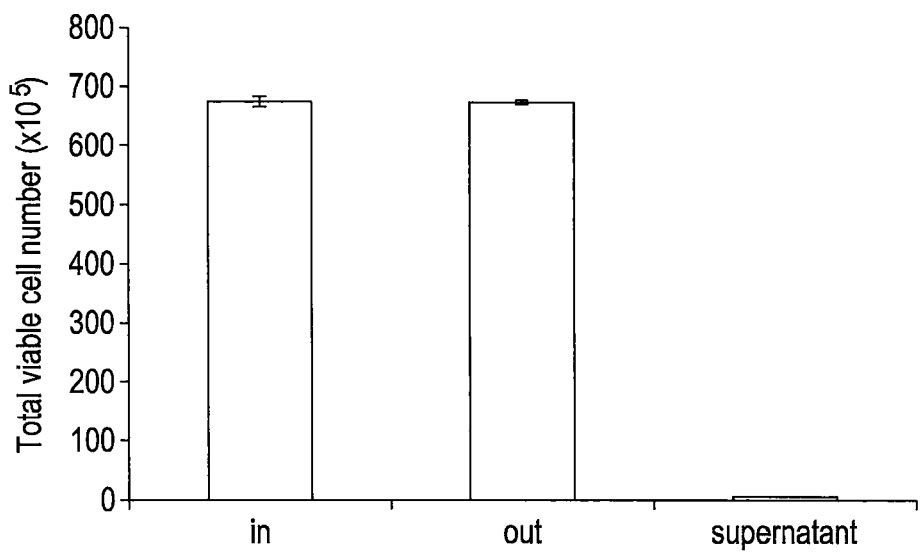
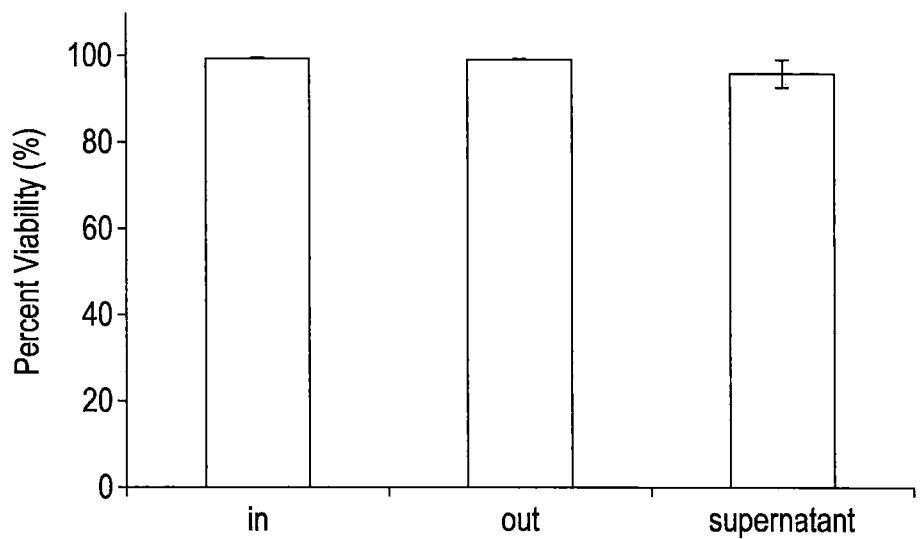
Fig. 10

Increase surface area and mixing with internal plates
Perforated plates
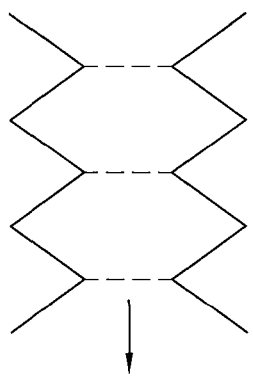
Baffles
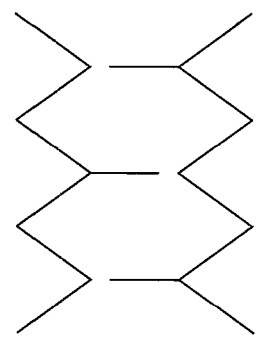
Cross section options include
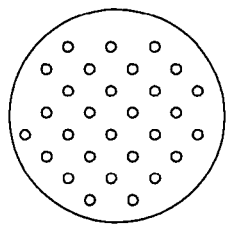 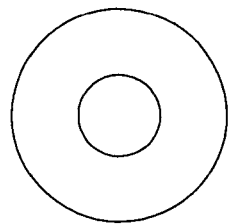 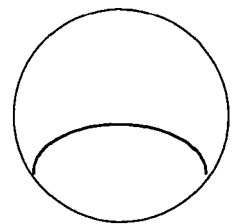
Fig. 16

CELL CULTURE DEVICE, SYSTEM AND METHODS OF USE THEREOF

The present invention relates to a device for culturing, manipulating or storing cells, including systems using such devices and methods of use thereof. The invention relates to methods of expansion of cells in culture and cryopreservation, as well as to methods of delivery of cells to subjects, including methods of obtaining a biological sample using such devices.

The culture or processing of cells typically requires the use of a device to hold the cells, for example in an appropriate culture medium when culturing the cells. The known devices include shaker flasks, roller bottles, T-flasks and bags. Such bottles or flasks are widely used but suffer from several drawbacks. Chief among the problems are the requirement for transfer of cells without contamination when passaging or processing subsequently.

The existing cell culture devices require re-supply of culture medium and oxygen for continued cell growth. Gas permeable cell culture devices are described in U.S. Pat. No. 8,415,144. However, such devices also require transfer of medium and/or cells in and out of the devices.

Collapsible devices for use in medicine are known; see for example U.S. Pat. No. 4,867,172 concerning a blood collector, or WO 2008/030597 concerning a canister liner for fluid collection. However, such devices are not fabricated or constructed for use in cell culture.

A key limiting factor in the production of cells for use in medicine is the absence of fully closed systems for processing of cells without contamination. For example during culture or subsequent processing of cells there is a risk of contamination when making additions to the culture vessel, or when removing cells. The operating systems are largely manual and hence expensive to operate. Furthermore with increasing manual operations comes increasing risk of manual errors and therefore the current labour-intensive processes lack the robustness required for the manufacture of clinical-grade therapeutics.

There is therefore a need for cell culture devices which permit such processing which avoids the requirement for constant passaging of cells into fresh culture devices, enables easy genetic modification of cells and simplifies handling of the cells in subsequent steps (such as washing etc.) and/or clinical use. For example, it would be advantageous if scale-up of cells in culture could be achieved without transfer of cells into a larger device as the cell population for any given culture increases.

According to a first aspect of the invention there is provided a cell culture container having a base section, a top section arranged in parallel with the top section and a wall element arranged between the top section and the base section and defining an internal lumen of the container, in which the wall element of the container is compressible with respect to the top and bottom section, and in which the top section of the container has an optionally sealable inlet, in which the wall element of the container is composed of a flexible material.

In one embodiment the wall element comprises a plurality of lateral rigid sections in the wall arranged in parallel with the base section where each pair of lateral rigid sections is interleaved with a deformable region. In another embodiment the wall element comprises a rigid helical coil region having a deformable region provided either side of the helical coil region.

In another embodiment, the top section, the base section and wall element may form a bag which can be held within an external adjustable frame, or in which the bag comprises an internal adjustable frame within the material of the bag.

The container of the invention is adjustable and may adopt a number of different configurations. It may be compressed from an expanded or partly expanded state or expanded from a compressed or partly compressed state. The different configurations may be achieved passively or actively, e.g. manually or under the control of an actuating device. The actuating device may operate in a reversible manner so as to cause the compression or expansion of the container as desired or required.

The container is compressible from an open arrangement in which it is fully extended, through semi-open or semi-closed arrangements, in which it is partly compressed or collapsed, to a fully collapsed or compressed arrangement.

The container is compressible with respect to the top and bottom sections where the wall element is deformable. The compression of the container is analogous to that of a concertina or bellows. The top section and bottom section are brought closer together by the deformation of the wall element. The deformation may occur along lines or zones of greater flexibility in the flexible material of the container.

The compression of the container may therefore also be described as being along an axis tangential to the plane of the top section and the bottom section. Thus if the top section and the bottom section are arranged in substantially horizontal positions (where the container can be described as being in an upright configuration) the compression of the container occurs in a vertical sense. Likewise, if the top section and bottom section are arranged in substantially vertical positions (where the container can be described as being in a transverse or lateral configuration) the compression of the container occurs in a horizontal sense In the fully extended or open arrangement, the container has a maximum available volume for culture of cells. In the fully collapsed or compressed arrangement the container has a minimum available volume which is more suitable for storage or transport of the container, or as part of a step in processing cells by washing or pelleting cells. The container may be compressed by means of an actuating device which brings the top section and base section closer together. Likewise, the container may be expanded by means of an actuating device which moves the top section and base section further apart.

Where the container is expanded from a closed or semi-closed arrangement, the expansion can be suitably controlled by means of manual expansion of the container, or a mechanical expansion where the container is held within an actuating device that expands the container by moving the top section and the base section further apart. The container may also be capable of self-expansion in some embodiments where the container is fabricated from a suitable material. The container may also be expanded by means of introducing a fluid such as a liquid or a gas. Likewise the container may also be compressed by means of removing a fluid such as a liquid or a gas.

The container may comprise a single internal lumen comprising a single chamber, or it may be divided by one or more closure means so as to form a plurality of sequentially arranged internal chambers within the internal lumen. In this way, the container can accommodate a number of different zones or regions in which different processes can occur either sequentially and/or in parallel when the container is in use. The plurality of chambers within a single closed-container system enables the simultaneous processing of multiple cell types each within their own chamber, with mixing only occurring if and when required.

The container can be adjusted to provide such different chambers by selective opening and closing of regions in the container as described herein. Where the container comprises a plurality of lateral rigid sections the movement of the individual sections can be independently controlled thus permitting one or more pairs of sections to be opened while others remain closed.

Each pair of lateral rigid sections may define an individual segment in the container. The container may therefore comprise several regions made up of one or more segments. The ability to open or close different segments or regions defining several segments selectively is an advantage of this aspect of the invention.

The top section and/or base section and/or wall elements may have inlet and/or outlet ports.

In this manner, a container of the invention can be used to process cells by moving the cells through the device by selectively opening and closing different segments or regions. The action of selectively opening or closing different segments or regions enables the volume and available surface area to be increased or decreased as desired according to the process being undertaken. The action of opening a segment or region may cause cells in culture to be moved from one chamber to another within the lumen of the container, or the cells in culture may also be mixed (e.g. after centrifugation). Cells can be moved in any direction depending upon the phase of the segments i.e. open or closed. Likewise the action of closing a segment or region may cause movement of cells and/or mixing. Full compression of the container may cause the cells in culture to be expelled from the container. Opening of the container from a closed arrangement when attached to or adjacent to a source of cells or liquid may cause liquid or cells to be drawn up into the lumen of the container where the container is suitably modified to receive such material or liquid via a cannula.

A plurality of lumens may also be formed by the action of heat-sealing across a suitable locus around the wall of the container thus annealing the walls of the container to form a seal. Such sealing may permit the selective removal of a part of a container containing cells or medium for storage (i.e. cryopreservation) and/or transport and/or waste removal (spent media) and/or cell selection.

In one embodiment of the invention, the container may comprise a plurality of chambers disposed within the lumen of the container along the axis of the container perpendicular to the orientation of the base section and the top section. The plurality of chambers may have different widths, i.e. the chambers may be evenly or unevenly sized. The chambers may each independently be in fluid communication, or alternatively the chambers may each independently be in re-sealable fluid communication. Thus one or more chambers may be selectively isolated from one or more other chambers. Having chambers of different volumes within the single device enables a range of operations to be carried that require either a specific cell or reagent density. For example, transfection and electroporation both require a high density of cells in a low volume; and inoculation requires a low density of cells in a large volume. Likewise for expensive reagents that need to be at a specific concentration to work efficiently, smaller volume chambers with higher cell density are more cost efficient.

In such embodiments, a population of cells can be introduced through the top section of the container of the invention and subjected to processing in a first chamber, followed by selective closing of the first chamber and the selective opening of an adjacent second chamber coterminous with the closing of the first chamber thereby moving the cells into the second chamber for subsequent processing. For example, the first chamber may be used to transfect the cells where the first chamber has a relatively small available volume and the second chamber may have a greater available volume for culture and expansion of the transfected cells, whereby additional culture medium can be supplied if required. More chambers can therefore be formed as necessary according to the processing method to be adopted where the overall dimensions of the container can be chosen accordingly.

The container may be composed of the same flexible material throughout. However, the top section and the bottom section may be composed of material which is different to that of the wall element. The material used in the top section and the bottom section may be less flexible than that of the wall element since in use it is not required to be compressed or expanded. The material may be a rigid material so that these sections have more structural rigidity. In some embodiments, the top section may be composed of a different material to that of the bottom section. In other embodiments, all parts of the container may be composed of the same flexible material.

The top section and the bottom section may be composed of a metal such as stainless steel (See FIG. 12 where metal is required to produce an electroporation chamber within the container, alternatively any generally suitable plastic material for use in cell culture, processing and storage (e.g. cryopreservation), such as polyethylene (high-density or low-density polyethylene HDPE or LDPE), polyvinylchloride (PVC), polypropylene (PP), polystyrene (PS) including high impact polystyrene, polyamides (PA), acrylonitrile butadiene styrene (ABS), polycarbonate (PC), polycarbonate/acrylonitrile butadiene styrene (PC/ABS) etc.

The flexible material may be a gas permeable material. The flexible material may be a plastic material. The flexible material may be a polyethylene (optionally a low-density polyethylene (LDPE)), cis-1,4-polybutadiene, a methacrylate such as poly (ethyl methacrylate), a phthalate such as poly (ethylene terephthalate), poly (vinylidiene chloride), a cellulose acetate such as cellulose acetate butyrate, a silicone, flouroethylenepolypropylene, polyolefin, or ethylene vinyl acetate copolymer.

The container is suitable for cell culture and processing of cells, including the use of the container in cell therapy, gene therapy vector production and/or exosome production. The container may be suitably sterilised prior to use (e.g. by gamma irradiation or other means). Optionally the internal surface of the device may be coated with or comprise biologically active agents which can act on the cells in culture and/or induce differentiation.

The base section may comprise an outlet, each outlet and inlet may be adapted for connection to a connector, for connection to a second collapsible cell culture device, or fitted with an adjustable or removable closure means, or a removable microporous filter. The base section may comprise a collection region. The base section may be substantially planar (horizontal) or it may be configured to be angular in cross-section, for example it may have a collection region to collect cells through settling in the device.

Where the container has a plurality of lateral rigid sections there may be of from 2 to 3, 2 to 4, 2 to 5, 2 to 6, 2 to 7, 2 to 8, 2 to 9, or 2 to 10, sections or more. The number of lateral rigid sections may be 2, 3, 4, 5, 6, 7, 8, 9, 10, or greater. In some embodiments the number of lateral rigid sections may from 10, 20, 30, 40, 50, 60, 70, 80, 90 or 100, or greater. The minimum number of lateral rigid sections in such an embodiment is 2 in which the top section comprises a lateral rigid section and the base section comprises a lateral rigid section with a deformable region interposed between. The lateral rigid sections may be composed of a reinforced section of material compared to the deformable regions in the wall of the container, such as a wire frame.

The container may be of circular, square, rectangular, elliptical, or triangular cross section. Alternatively, the container may comprise a number of different sections or regions of a variety of cross sections, such as for example a series of circular cross sections with variable (increasing and/or decreasing) diameters.

The cell culture containers of the invention may be adapted to permit partial occlusion between individual segments or sections/chambers within the lumen of the container whilst still permitting liquid flow between segments or sections/chambers.

For example, the lumen of the container may comprise a plurality of connected chambers wherein each chamber is composed of a series of segments formed from pairs of lateral rigid sections.

The plurality of connected chambers can further be provided with a releasable closure means at either end of each the plurality of connected chambers. The closure means may be a clamp. In other embodiments, the chambers can be permanently sealed using a heat sealer or similar to cause a welding of the wall element at a desired location so that an individual chamber (section) can be removed from the container.

The cell culture containers of the invention can be provided with a membrane or filter located within the lumen at the deformable region to partition the lumen into a plurality of segments formed from pairs of lateral rigid sections. The membrane or filter can be perforated by one or more holes.

The membrane or filter can semi-partition the lumen up to 35%, 40%, 45%, 50%, 55%, 60%, 65%, 70%, 75%, 80%, 85%, 90%, 95%, or 99% or 100% of the available surface cross-sectional area of the lumen.

The membrane can be non-contiguous (i.e. the membrane does not wholly partition the lumen) with the wall element and thus form a series of baffles arranged within the internal lumen. For example, the baffle elements may be arranged at alternate lateral rigid sections or at each lateral rigid section.

The material of the membrane or filter can be the same or different as the material forming the wall element. The membrane may be a cellulose, e.g. nitrocellulose membrane. The filter may be a microporous filter. The membrane or filter may be releasable.

The cell culture container of the invention may have a plurality of internal wall elements arranged concentrically within the lumen of the chamber.

In this embodiment, the container may also be provided with series of concentric internal surfaces with decreasing cross-sectional area, but which do not absolutely partition the internal lumen. In such an embodiment, the container comprises a series of nested wall elements arranged concentrically with reducing cross sectional areas. However, liquid flow is possible around and throughout the internal lumen of the container in order to permit cells in culture to be attached to all available surfaces. The arrangement need not necessarily be circular and other regular geometric shapes are possible. The only requirement is that each smaller nested surface fits within the preceding larger nested surface up to the wall element of the container.

Each lateral rigid section may be of the same or different cross-sectional area as the deformable region. In this manner, the container may be composed of a series of interlinked chambers with increasing or decreasing volume and surface area.

The base section may be frusto-conical in shape having a substantially planar horizontal base region. The base section may be configured to engage with a delivery mechanism for release of cells from the container, such as in a method of administration of cells to a subject as described herein. An outlet may therefore be provided in the base section also to permit such release or administration. Where an outlet is present, it may be adapted to accept a cannula suitably by means of a Luer lock connector ("Luer-Lok™"). The outlet may be sealable with an adjustable and/or removable closure means.

The top section may be frusto-conical in shape. The inlet in the top section may be adapted to accept a cannula suitably by means of a Luer lock connector. The inlet in the top may be sealable with an adjustable and/or removable closure means, or provided with a removable microporous filter. The top section may be substantially planar (horizontal) or it may be configured to be angular in cross-section.

Each inlet and outlet may independently function in the reverse manner as required. References to a cannula include any type of needle used in delivery of cells or fluids to a subject, or used in obtaining samples of biological material or liquid from a subject. Where present, the cannula is in fluid communication with the internal lumen of the container.

This aspect of the invention extends to a cell culture container comprising cells in culture and cell culture medium. The cell culture container comprising cells may be frozen.

In this aspect of the invention, cells may be cultured in the cell culture container of the invention. The cells may be in suspension culture or attached to a substrate. The substrate may be removably affixed to one more internal surfaces in the lumen of the container, or removably affixed to microparticles. The cells may be subjected to mixing, or centrifuging, followed by re-suspending in fresh medium. The flexible material of the collapsible cell culture container may be gas permeable which can enable gas transfer to supply gas, for example oxygen, to the cells.

In order to increase the scale of any given culture, the cell culture container may be extended from closed or semi-closed arrangement in which the cell culture container is collapsed in full or in part to an open or semi-open arrangement in which the cell culture container is extended.

As can be seen from the above, the cell culture container may have a variety of orientations and arrangements. It is suitable for multi-step processing of cells as described herein as well as for increasing scale of cell culture. The container may comprise a single chamber or multiple linked chambers in which different processing steps, suitably sequentially.

According to a second aspect of the invention there is provided a method for culturing cells in a cell culture container having a base section, a top section arranged in parallel with the top section and a wall element arranged between the top section and the base section and defining an internal lumen of the container, in which the wall element of the container is vertically compressible with respect to the top and bottom section, and in which the top section of the container has an optionally sealable inlet, in which the container is composed of a flexible material, comprising culturing cells in a culture medium in the cell culture container. Other features and aspects of the container may be as defined herein.

The method may further comprise one or more steps of washing, separating and/or cryopreserving the cells. The steps may take place in any order and be repeated as desired.

In this aspect of the invention, the method may additionally comprise centrifuging the cell culture container to form a pellet of cells, the supernatant liquid may be displaced by collapsing the cell culture container (by collapsing the container in the manner of closing an open concertina), followed by re-suspending the cell pellet, suitably by re-opening the container in the manner of opening a closed concertina. The culture of cells in the collapsible cell culture container may be subjected to freezing (e.g. cryopreservation) for transport or storage, or further culturing, including optional activation steps or processing and subsequent administration to a subject.

The culturing of the cells may include the step of transfection of the cells in order to introduce a heterologous nucleic acid (genetic material) into the cells which may be in the form of a nucleic acid sequence, optionally contained in a vector, which may encode a protein or RNA sequence of interest with accompanying regulatory and control elements with respect to gene expression such as a promoter. The nucleic acid sequence may be DNA or RNA. The step of transfecting the cells may suitably occur in a small volume of liquid. In such a process, the amount of liquid present can be reduced by removal of excess liquid through an outlet in the container.

Where the container comprises a number of discrete separate chambers within the lumen of the container, the step of transfection can take place in a designated region of the chamber which is arranged so as to hold a reduced volume of liquid in order to facilitate the transfection of the cells.

Different processing steps can therefore be arranged to take place in different chambers within the container which can be formed by selective opening and closing of regions in the container as described herein.

The cell culture container may be used to culture any prokaryotic or eukaryotic cell, suitably an animal cell, e.g. a mammalian, cell. The cells may be human or non-human. Examples of sources of suitable non-human cells include, rodents such as mice, rats, and guinea-pigs, as well as ungulate animals selected from ovine, caprine, porcine, bovine and/or equine species, or non-human primate species. However, the cells may be bacteria, yeast, fungi or plant cell in origin also.

The cells may be of any type including somatic cells and non-somatic cells. The cells may be stem cells derived from any stage of development of the embryo, foetus or adult animal. The cells may be genetically modified cells, such as chimeric antigen receptor T-cells (CARTs). The cells may be from a deposited cell line, such as genetically-modified Chinese Hamster Ovary (CHO) cells to produce recombinant proteins.

For example, embryonic stem (ES) cells, including cells of non-human origin. The cells may be derived from a deposited cell line, such as an ES cell line, or cells of a cancer or a hybridoma which can be caused to proliferate in culture and/or produce monoclonal antibodies. The cells may also be derived from the result of somatic cell nuclear transfer (SCNT) in which the nucleus of a somatic cell is placed into an enucleated oocyte.

The cells may be pluripotent stem cells, for example primate pluripotent stem (pPS) cells, for example human embryonic stem (hES) cells. Where the cells are stem cells, the source may be from any tissue of the body, including mesenchymal stem cells (including umbilical cord derived stem cells), neural stem cells or haematopoietic stem cells. Also included are induced pluripotent stem (iPS) cells.

According to a third aspect of the invention there is provided a method of treating a medical or veterinary condition in a subject comprising administering cells to the subject from a container having a base section, a top section arranged in parallel with the top section and a wall element arranged between the top section and the base section and defining an internal lumen of the container, in which the wall element of the container is vertically compressible with respect to the top and bottom section, and in which the bottom section is provided with a cannula, in which the container is composed of a flexible material. Other features and aspects of the container may be as defined herein. In some embodiments, the top section of the container may be provided with an optionally sealable inlet.

The method of treatment of a medical or veterinary condition can include cell therapy by way of administration of cells, including genetically modified cells, to a subject in need thereof. Likewise a method of treatment of a medical or veterinary condition can include products produced by the cells including exosomes, conditioned media, monoclonal antibodies and recombinant proteins, to a subject in need thereof.

The cosmetic treatment can include any non-therapeutic method of treatment which provides a cosmetic (aesthetic) enhancement by way of administration of cells to a subject.

The cells may be cultured in a cell culture container according to the first aspect of the invention prior to administration, including optionally washing and re-suspending the cells in the container.

In this aspect of the invention, the container may optionally comprise a cryopreserved population of cells in the cell culture container which are subsequently thawed prior to administration. Suitably the thawed cells may be resuspended in a physiologically acceptable medium before use. The cells can be further washed, centrifuged and resuspended in the container again if required. The physiologically acceptable medium may be any generally acceptable buffer, adjuvant and/or diluent as required for the final formulation to be administered to the subject. For example, the medium may be phosphate buffered saline (PBS), suitably at pH 7.4.

The cells may be administered from the cell culture container in the form of an injection. The cell culture container is provided with a cannula for administration of the cells, for example by means of a Luer lock connector. The cell culture container may be provided with an actuator means for delivery of the cells. The actuator means may comprise a lever or other means providing a force to compress the container which can function as in the action of a syringe device. The actuator may be manually operated or operated controlled by an external electrical control system. The actuator means can therefore act as a compacting mechanism which acts to control the collapse of the cell culture container to cause the exit of the cells from the container into the subject through the cannula.

The cells may also be administered by way of an infusion from the cell culture container, in which the cell culture container may be expanded to its greatest extent. In this embodiment, the cells may be suspended in a greater volume of medium as appropriate. The infusion may be administered passively, by a bidirectional linear actuator (e.g. syringe-driver-like device) operating under the control of an external electrical system may be provided as required or necessary for greater control.

According to a fourth aspect of the invention there is provided a method of obtaining a biological sample from a subject comprising inserting a cannula into the subject in which the cannula is disposed within a container having a base section, a top section arranged in parallel with the top section and a wall element arranged between the top section and the base section and defining an internal lumen of the container, in which the wall element of the container is vertically compressible with respect to the top and bottom section, and in which the bottom section of the container is provided with the cannula, in which the container is composed of a flexible material, in which said container is operatively connected to an actuator means for expanding the container thereby removing the sample from the subject. Other features and aspects of the container may be as defined herein. In some embodiments, the top section of the container may be provided with an optionally sealable inlet.

The actuator means can open the container from a closed or semi-closed arrangement in order to permit ingress of the sample into the lumen of the container. The actuator means may comprise a lever or other means providing a force which can expand the container as in the action of a syringe or other biopsy device. The actuator may be manually operated or operated controlled by an external electrical control system.

The cannula of the container may be inserted into to a blood vessel or bone marrow cavity. The container may be used to obtain cells, for example stem cells, from the subject such as blood, bone marrow, umbilical cord, adipose tissue, amniotic fluid etc. which can be conveniently biopsied in this manner.

Preferred features for the second and subsequent aspects of the invention are as for the first aspect mutatis mutandis.

The present invention therefore provides for the single chamber processing of cells with multiple unit processes taking place as desired without movement of cells and/or media between separate containers or devices thus also avoiding the risk of contamination. The system is simpler to use and further avoids the complexity of existing approaches. The invention provides for the safer processing of cells with improved reproducibility and ease of use.

The invention also provides for the extraction of cells from a patient (biopsy, such as blood or bone marrow), separation of cells, processing of cells (including cytokine stimulation and/or genetic modifications), solid-liquid separations and loading into a delivery device where the cells can be present in the same container throughout the entire process.

The invention will now be further described by way of reference to the following Examples and drawings which are present for the purposes of illustration only and are not to be construed as being limitations on the claimed invention. Reference is made to the following Figures also in which:

FIG. 1 shows a representation in a perspective view of one embodiment of the cell culture container of the invention in 3 separate arrangements in the upright configuration. FIG. 1(a) shows the container fully extended; FIG. 1(b) shows the container partly collapsed (partly extended); and FIG. 1(c) shows the container fully closed (fully collapsed).

FIG. 2 shows a diagrammatic representation in a plan view of a cell culture container of the invention in the upright configuration. FIG. 2(a) shows the container partly extended and FIG. 2(b) shows the container in a partly closed (collapsed) arrangement suitable for mixing cells in the container, such as by squeezing or compressing the container.

FIG. 3 shows a plan view of a cell culture container of the invention in which selected segments of the container are collapsed ("closed") in the upright configuration. FIG. 3(a) shows the lower segments and the bottom end of the container as fully closed; FIG. 3(b) shows the upper segments at the top of the container fully closed; and FIG. 3(c) shows the container fully extended at both ends.

FIG. 4 shows a diagrammatic representation of a processing scheme for using a cell culture container of the invention comprising centrifuging cells in the container, removing supernatant, re-suspending cells in fresh media and subsequent downstream processing such as freezing, thawing, cell culturing, cytokine stimulation, washing, administration to patient.

FIG. 5 shows a more detailed representation in diagrammatical form of how a cell culture container of the invention may be used to prepare cells for administration to a patient. The cells in the container may be frozen in situ in the container after optional centrifugation (as shown in FIG. 4), followed by thawing, centrifuging again (formation of cell pellet), re-suspending in buffer and then either injection or infusion of the cells into a patient. In the injection mode of administration, the cell culture container of the invention is inserted into a compression means (which may be power driven as shown for controlled rate delivery) and also fitted with a suitable cannula such as my means of a Luer lock connector for administration of the cells into the patient by the action of the compression means upon the container. In the infusion mode of administration, the container is used as a reservoir for infusion according to any generally convenient approach for such procedures.

FIG. 6 shows alternative embodiments and uses of the containers of the invention in which FIG. 6(a) shows the cell culture container being used as a "shaker flask"; FIG. 6(b) shows the cell culture container being used as a "roller bottle"; and FIG. 6(c) shows the cell culture container with the form of a "T-flask.

FIG. 7 shows alternative configurations of the containers of the invention in which FIG. 7(a) shows a side view of a cylindrical container composed of a flexible material scored to file in a specific location in which rigid wires provide a flexible construction with a wire frame; FIG. 7(b) shows another embodiment in which the container has a collapsible helical screw region in the form of a "concertina"; and FIG. 7(c) shows top views of various containers of the invention with different shapes.

FIG. 8 shows an alternative embodiment of a container of the invention in side view and a cross section view through the top. The container comprises a plurality of concentric internal surfaces radiating from the central axis out to the external wall. The multiple internal surfaces therefore act as additional locations for cells to attach in attached cell culture. Culture media are able to flow freely around the surfaces and to circulate within the device.

FIG. 9 shows three day batch cultures in shaken containers of the invention. Cell growth in FIG. 9(a) and viability FIG. 9(b) have been plotted against time. All cell concentrations and viabilities were measured by trypan blue. Each data point represents the mean value of three replicates (n=3). Error bars represent one standard deviation above and below the mean.

FIG. 10 shows centrifugation and re-suspension of cells in containers of the invention. FIG. 10(a) shows the total number of cells in suspension prior to centrifugation (in) the total number of cells post centrifugation and resuspension in fresh medium (out) and the total number of cells in the clarified supernatant. FIG. 10(b) shows the corresponding viabilities. Each data point represents the mean value of three replicates (n=3). Error bars represent one standard deviation above and below the mean.

FIG. 11 shows a full sequence of common cell processing operations in a single container. As shown in FIG. 11(a) cells were inoculated into the container, grown for 24 hours before being pelleted by centrifugation. The pellet was resuspended in freezing medium and frozen at −80° C. for 24 hours. Finally the frozen cell suspension was thawed in a 37° C. water bath, pelleted by centrifugation and resuspended in fresh medium. At no point during this sequence were cells removed from the container. The only flow of material in and out of the concertina was the removal of supernatant post centrifugation and the addition of freezing medium/fresh medium for resuspension of pellets during the two washing steps. FIGS. 11(b) and 11(c) shows the total viable cell number and the viability which was measured at key points during the process as indicated by numbers 1-4 on FIG. 11(a). Each data point represents the mean value of three replicates (n=3). Error bars represent one standard deviation above and below the mean.

Figure 15:
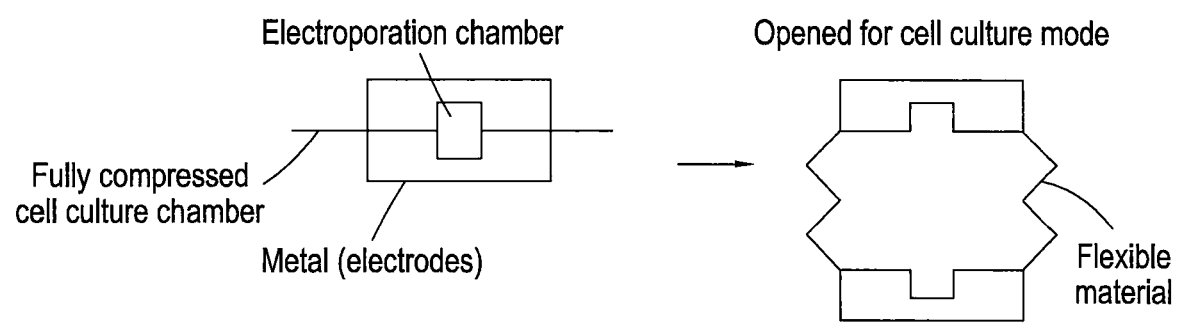

FIG. 15 shows the top and bottom made of metal in order to produce a chamber for electroporation. The metal at the top and bottom surfaces act as the two electrodes (positive and negative) with an insulator (the plastic wall) in between. Thus an electrical field can be applied to the cells in order to increase the permeability of the cell membrane, allowing chemicals, drugs, or DNA to be introduced into the cells Post electroporation, the chamber can then be expanded to enable for example cell culturing.

FIG. 16 shows an arrangement where the container is segmented by perforated structures (stacking disks) running across the lumen parallel to the top/bottom. This arrangement is analogous akin to a multi-stack cell culture device but has flexible walls between perforated discs that enable the flow of reagents, media and or cells by the compression and expansion of the chamber containing the stacked disks. The perforations can be any size, number or position. FIG. 16 shows variants of the containers of the invention that can increase surface area (e.g. for increased cell attachment), or increase mixing by acting as baffles, or enabling efficient centrifugation for example when pelleting cells.

DETAILED DESCRIPTION OF THE FIGURES

Figure 1C:
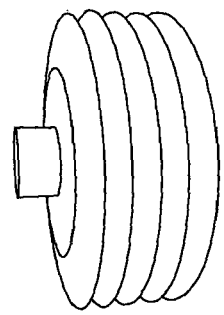
Figure 1B:
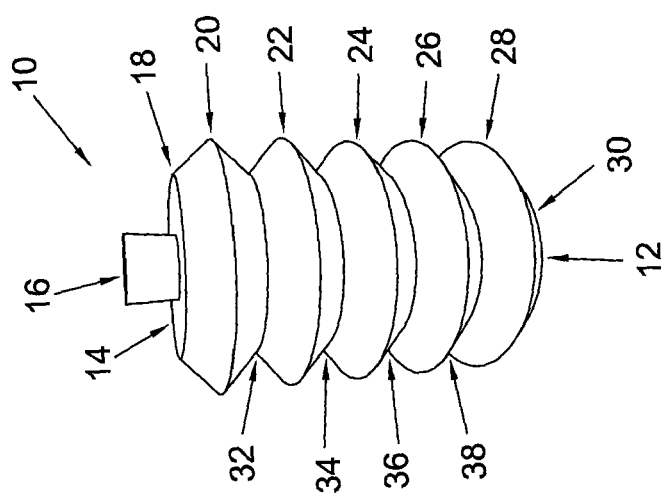
Figure 1A:
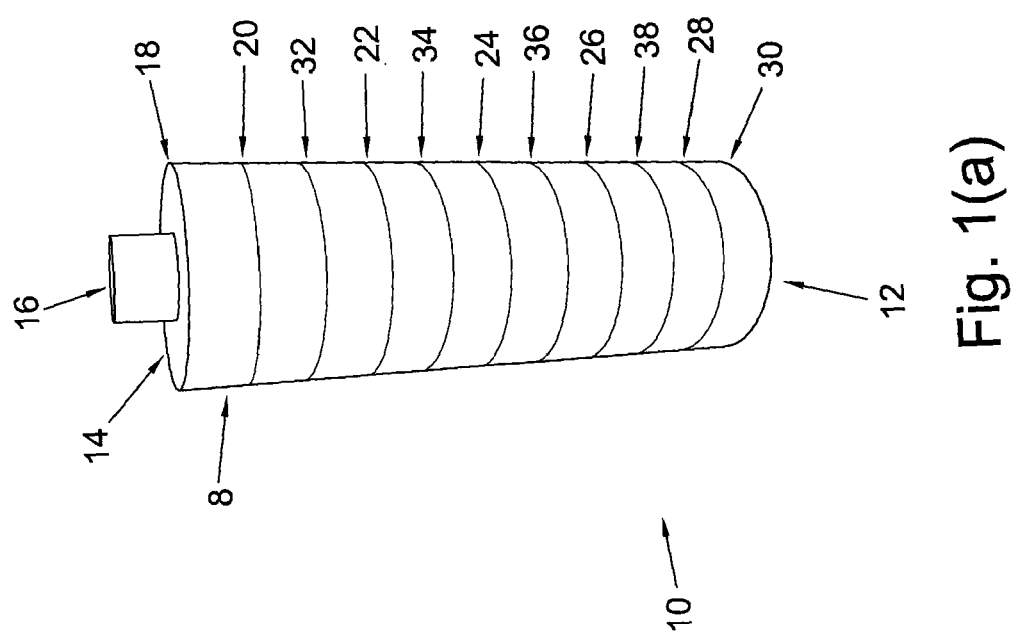
Figures 2A, 2B:
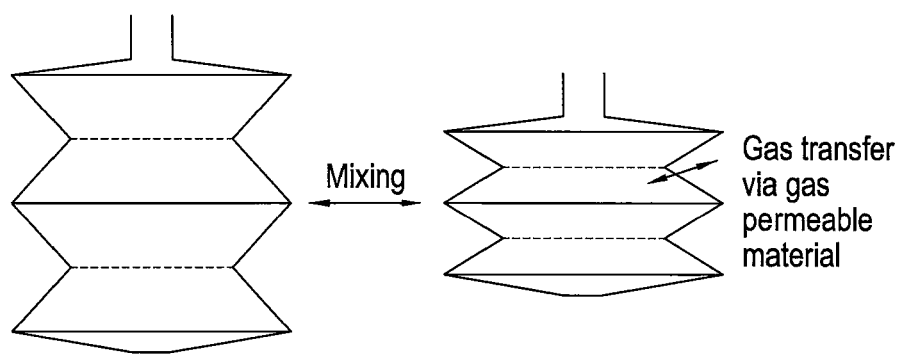
Figure 4:
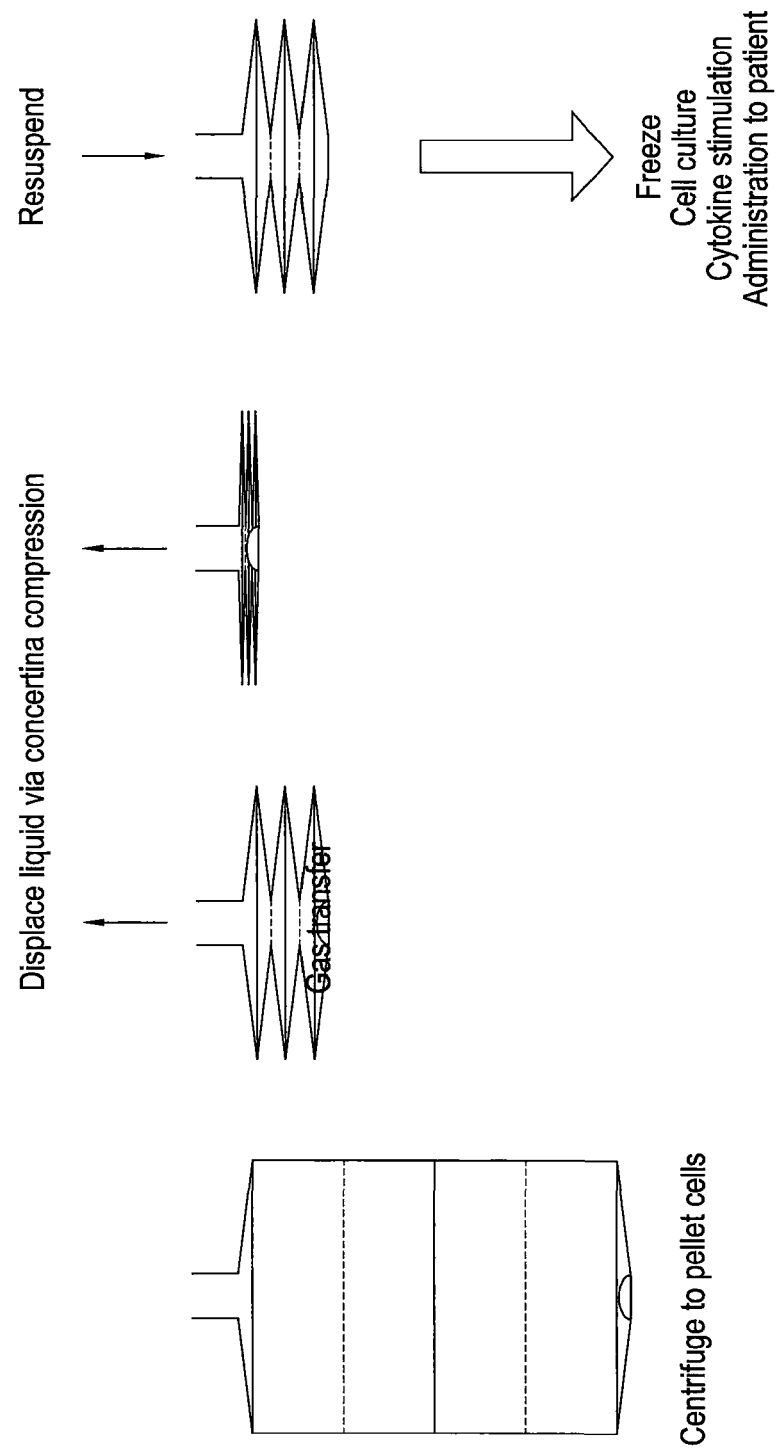
Figure 5:
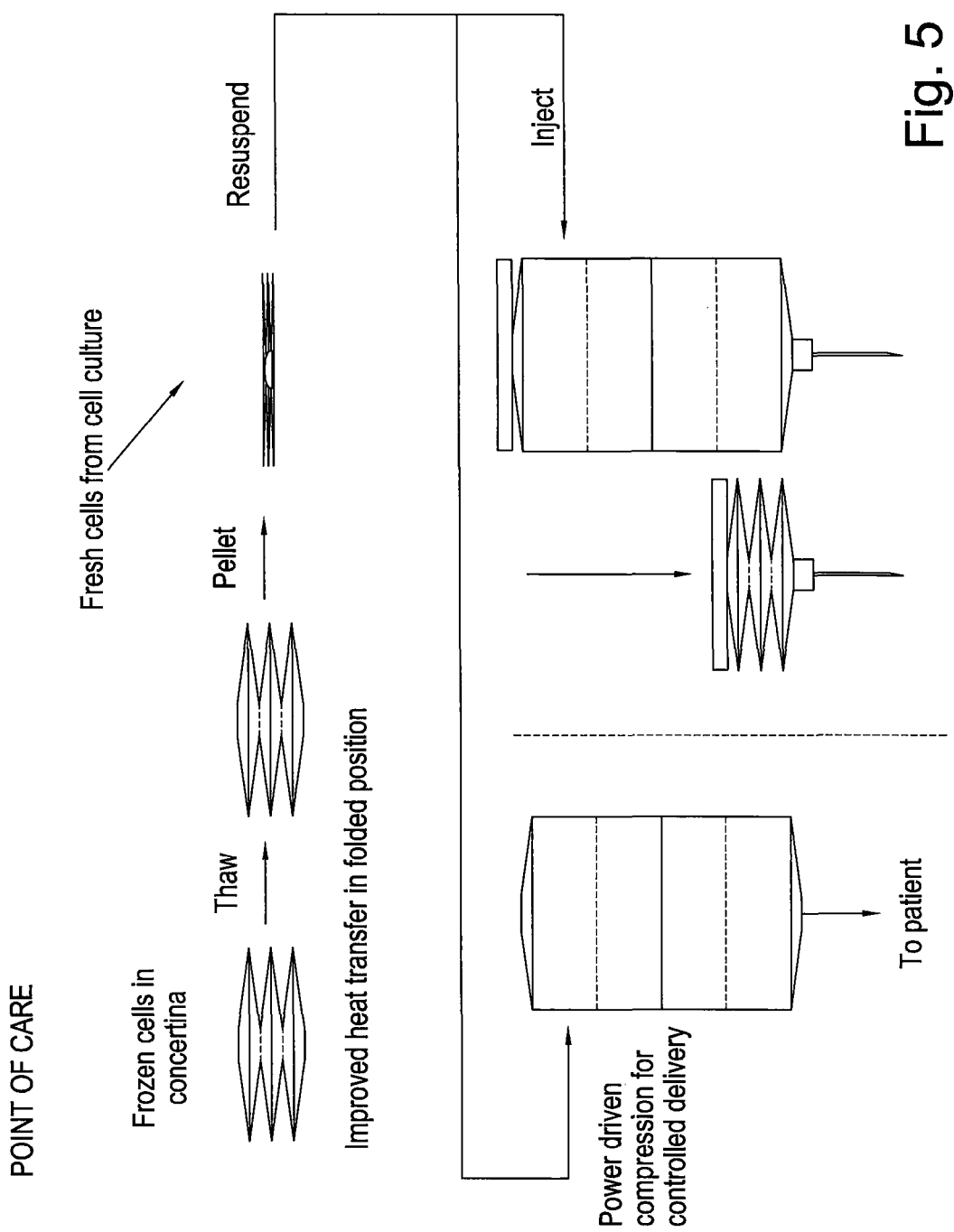

FIG. 1 shows one embodiment of a collapsible cell culture container (10) of the invention comprising a base section (12), a top section (14) and a wall element (8). The wall element (8) comprises annular rigid sections (18, 20, 22, 24, 26, 28, 30) laterally arranged in parallel with the base section (12). The top region (14) comprises annular rigid section (18) and the base region (12) comprises annular rigid section (30). The annular rigid sections and deformable regions may have the same or different diameters. The figure shows the container in the upright configuration. Each adjacent pair of intermediate annular rigid sections (18, 20, 22, 24, 26, 28, 30) is interleaved with a deformable region (32, 34, 36, 38). The action of a compressive downward force perpendicular to the vertical axis of symmetry of the container causes the container to collapse as shown in FIG. 1(b) to a partly closed arrangement and then to a fully closed arrangement as shown in FIG. 1(c).

The container has an inlet (16) as shown which may function as a removable closure means or temporary seal. In FIG. 1(a), the container is fully extended so the deformable regions may not necessarily be immediately visible. In FIG. 1(b), the container is partly collapsed, where the deformable regions are visible as zones in which the device has collapsed to form a "concertina" shape. In FIG. 1(c) the container is fully collapsed.

FIG. 3 shows further arrangements of a container (50) of the invention. The embodiment shown is a modification of the embodiment (10) of FIG. 1 in which the top region (14) and annular rigid section (18) as shown in FIG. 1 form a single fused top region (54, 58) in the container shown in FIG. 3. The annular rigid sections are shown in FIG. 3 as sections (60, 62, 64, 66, 68, and 70). The deformable regions are shown in FIG. 3 as sections (72, 74, 76, 78, 80). The container has a base (52), an inlet (56). The container according to FIG. 3 is shown as comprising two chambers: Chamber 1 and Chamber 2. In FIG. 3(a), Chamber 1 is open and Chamber 2 is closed. In FIG. 3(b), Chamber 1 is closed and Chamber 2 is open. In FIG. 3(c), both Chamber 1 and Chamber 2 are open. In such a manner, the container provides for multistep operation where media and cells can be moved from the open chamber to the closed chamber as shown (from FIG. 3(a) to FIG. 3(b) arrangements); or where the scale of the cell culture can be increased by opening both chambers.

The collapsible cell culture container as shown in FIG. 1 has an overall circular cross section and is based on a cylinder form. The containers of this aspect of the invention may suitable used as shaker flasks or roller bottles in place of traditional cell culture devices, see for example FIGS. 6(a) and 6(b). FIG. 6(c) shows an alternative aspect of a container of the invention which has an overall rectangular cross-section which takes the form of a T-flask and may be used in place of the standard T-flasks known in the art.

Figure 7A:
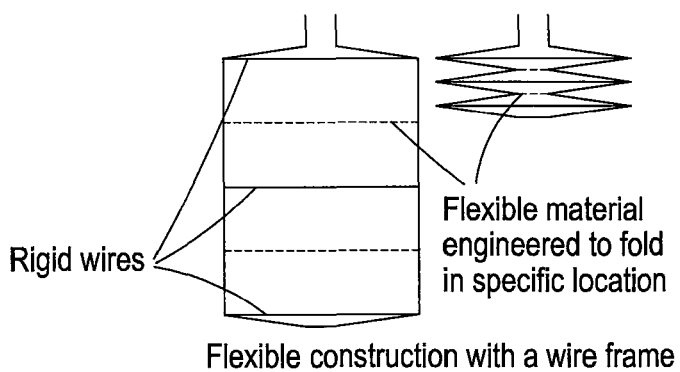
Figure 7B:
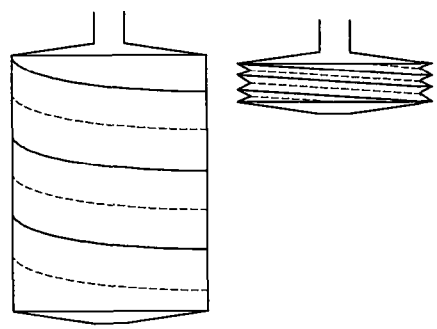
Figure 7C:
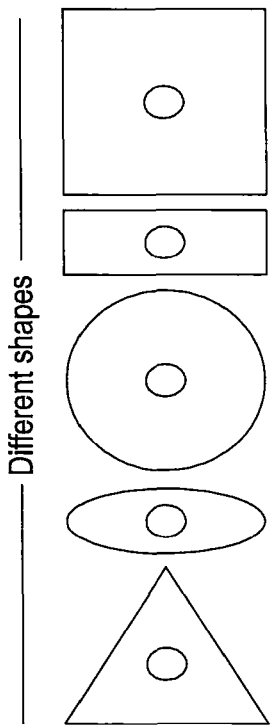

FIG. 7(a) shows in greater detail how the containers of the invention may be formed from flexible material scored to fold in a specific location, where rigid wires may be used in some embodiments to provide a flexible construction with a wire frame. FIG. 7(b) shows another embodiment in which the container is collapsible by virtue of a flexible helical screw region. FIG. 7(c) shows a plan view of containers of the invention having a variety of different cross sections based on the different geometric shapes as indicated. The cross section may be any suitable geometric shape, for example circular, square, rectangular, elliptical, or triangular.

FIG. 8 shows a container of the invention which comprises a series of concentric nested internal surfaces within the internal lumen of the container which provides for an increased surface area for attached cell culture. FIG. 8(a) shows a side view and FIG. 8(b) shows the cross section through the container as viewed from the top.

Figure 12:
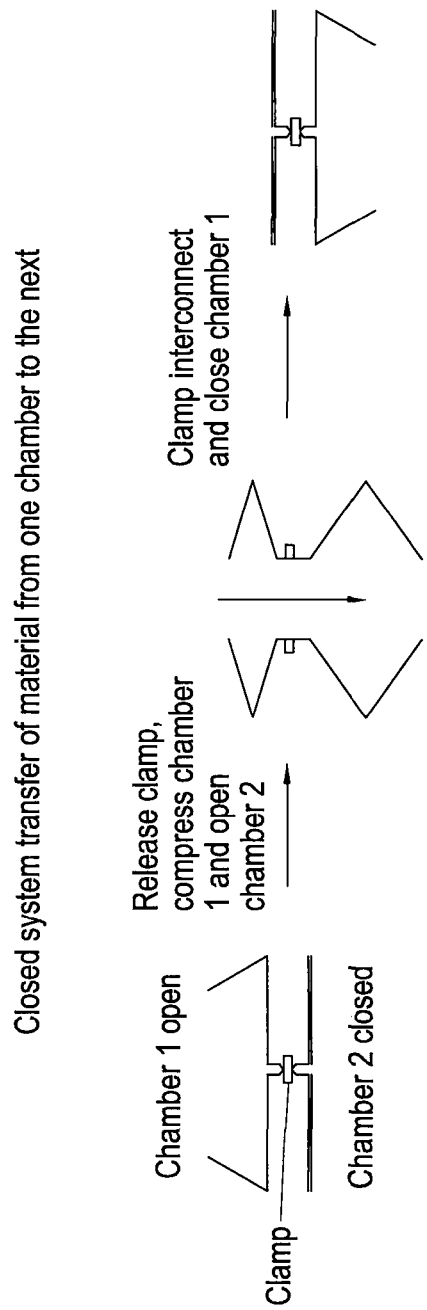
FIG. 12 shows a schematic representation of how the container of the present invention provides a closed system for the transfer of material from one chamber within the container to another chamber by selective opening and closing of separate segments within the container.

FIG. 12 shows how a container of the present invention provides a closed system for the transfer of material from one chamber within the container to another chamber by selective opening and closing of separate segments within the container. In the first arrangement, where "Chamber 1" is expanded ("open"), "Chamber 2" is compressed ("closed"

or otherwise not accessible from "Chamber 1") by means of a clamp. The clamp may be released as shown, followed by compression of "Chamber 1" to expel material from "Chamber 1" into "Chamber 2", after which the connection between the chambers can be closed by means of the clamp. In the final arrangement, "Chamber 1" is compressed ("closed") and "Chamber 2" is expanded ("open").

Figure 13:
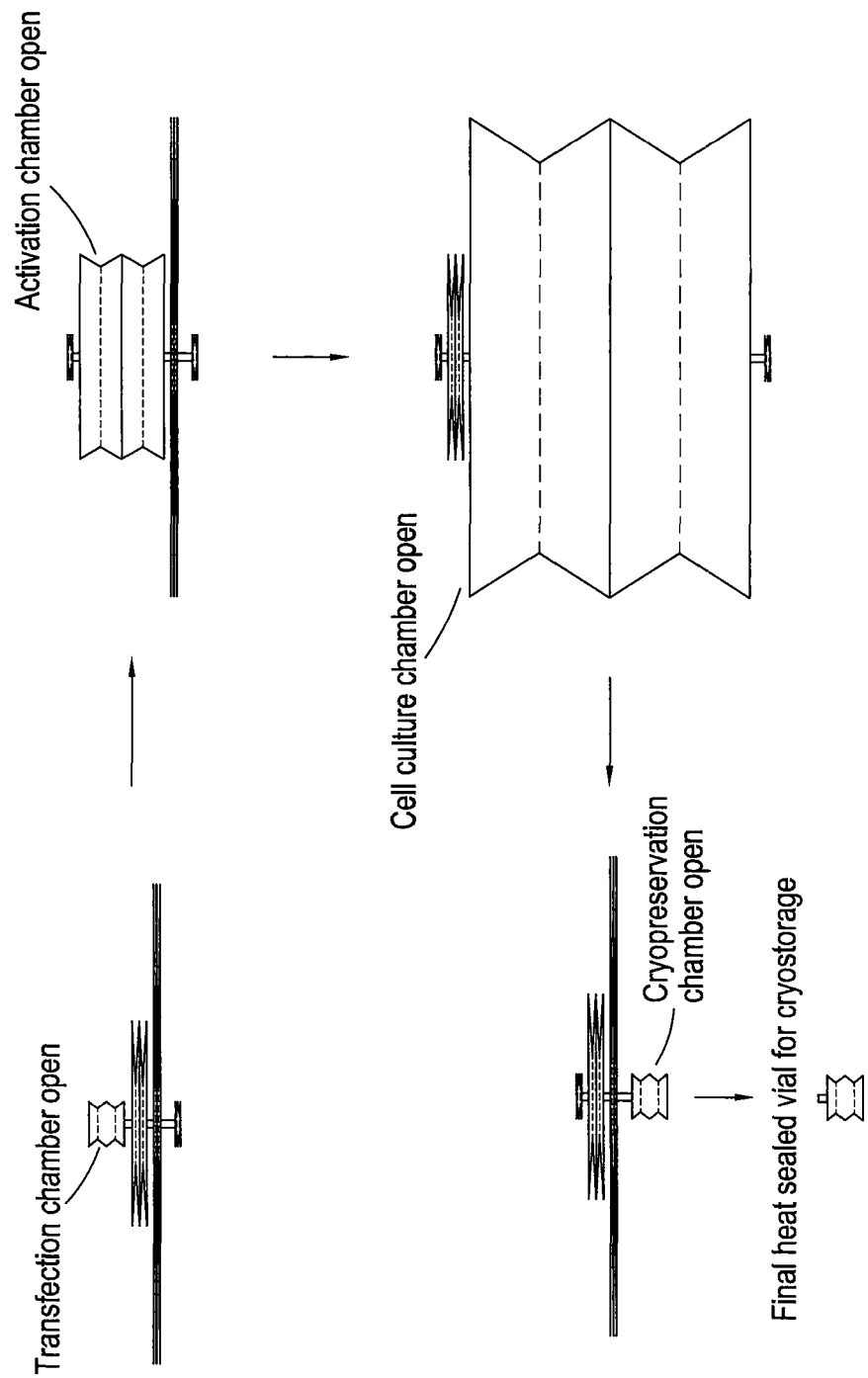
FIG. 13 shows a schematic representation of a multi-step process in a single closed container device, in which the container comprises 4 separate chambers: a transfection chamber; an activation chamber; a cell culture chamber; and a cryopreservation chamber.

FIG. 13 shows how a single container can be used to operate a multi-step process, such as in the manufacture of chimeric antigen receptor T-cells (CAR Ts). The container has 4 chambers as indicated each with different cross sectional areas. The container is shown with the transfection chamber expanded ("open") to allow for transfection of cells introduced into the chamber. After transfection process has been completed, the transfection chamber is selectively compressed ("closed") while expanding ("opening") the activation chamber. Subsequently, following activation the cells are moved on by selectively expanding ("opening") the cell culture chamber and compressing ("closing") the activation chamber. Once sufficient expansion of the cells in culture has occurred the cells are moved on into the cryopreservation chamber by selective compression of the cell culture chamber and selective expansion of the cryopreservation chamber. Finally, the cryopreservation chamber is removed by the action of heat-sealing the region between the cryopreservation chamber and the cell culture chamber. The cryopreservation chamber is then ready for cryopreservation and storage.

Figure 14:
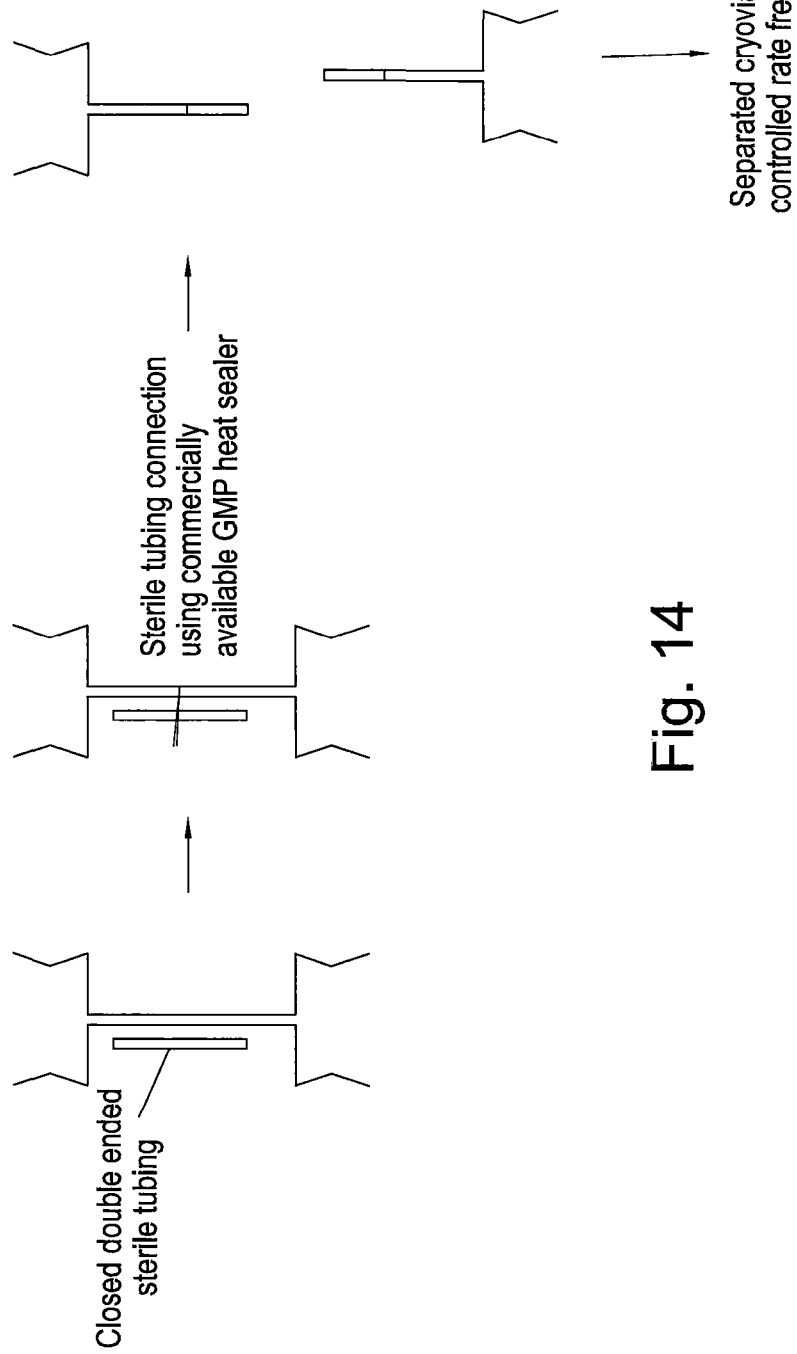
FIG. 14 shows the sterile separation of chambers in schematic form.

FIG. 14 shows how chambers within a container of the invention can be separated in a sterile manner, for example in the removal of a cryopreservation chamber as described in the scheme according to FIG. 13. FIG. 14 shows a container of the invention with two chambers joined together. Typically, the chamber to be removed will be the terminal chamber in a container, i.e. distal from the chamber at the end of the container where processing commenced (the proximal chamber). Closed double ended sterile tubing may be provided as indicated and arranged around the joint to be sealed and separated. A standard GMP heat sealer device may be used to seal the tubing and separate the chamber from the container. The separated cryopreservation chamber (cryovial) can then be removed and stored in a controlled rate freezer.

The invention therefore provides a collapsible cell culture container having a base section, a top section and a wall element arranged between the top section and the base section and defining an internal lumen of the container, in which the wall element of the container comprises (i) a plurality of lateral rigid sections in the wall arranged in parallel with the base section where each pair of lateral rigid section is interleaved with a deformable region or (ii) a rigid helical coil region having a deformable region provided either side of the helical coil region, and in which the top section of the container has an inlet, in which the container is composed of a flexible material.

Examples: Culture of Cells in Collapsible Cell Container

The processing of cells for therapeutic application is complex and labour intensive owing to the large number of complex steps involved. Here the inventors have invented and tested a new platform technology which can be used to carry out all of the steps involved in the production of a cell therapy without the cells ever leaving a single container. In these experiments a collapsible cylindrical concertina arrangement was used to enable exquisite control over volume:surface area ratio. Using this arrangement it was possible to culture cells, wash them via centrifugation and subject them to a freeze thaw cycle all in sequence without the cells leaving a single vessel.

For these experiments an off-the-shelf collapsible plastic concertina was used commonly used as a vacuum drainage kit in veterinary surgical procedures (Part number AD1 BC, Adhesive Dispensing Ltd). The vessels were 30 ml in volume and constructed from Polyethylene LDPE. With the concertina extended the device was used as a shaker flask for the expansion of suspension cells. The same concertina could be centrifuged resulting in the formation of a cell pellet. By collapsing the concertina the majority of supernatant could be squeezed from the container.

Example 1

Cell Culture in Concertina Device

Figure 9:
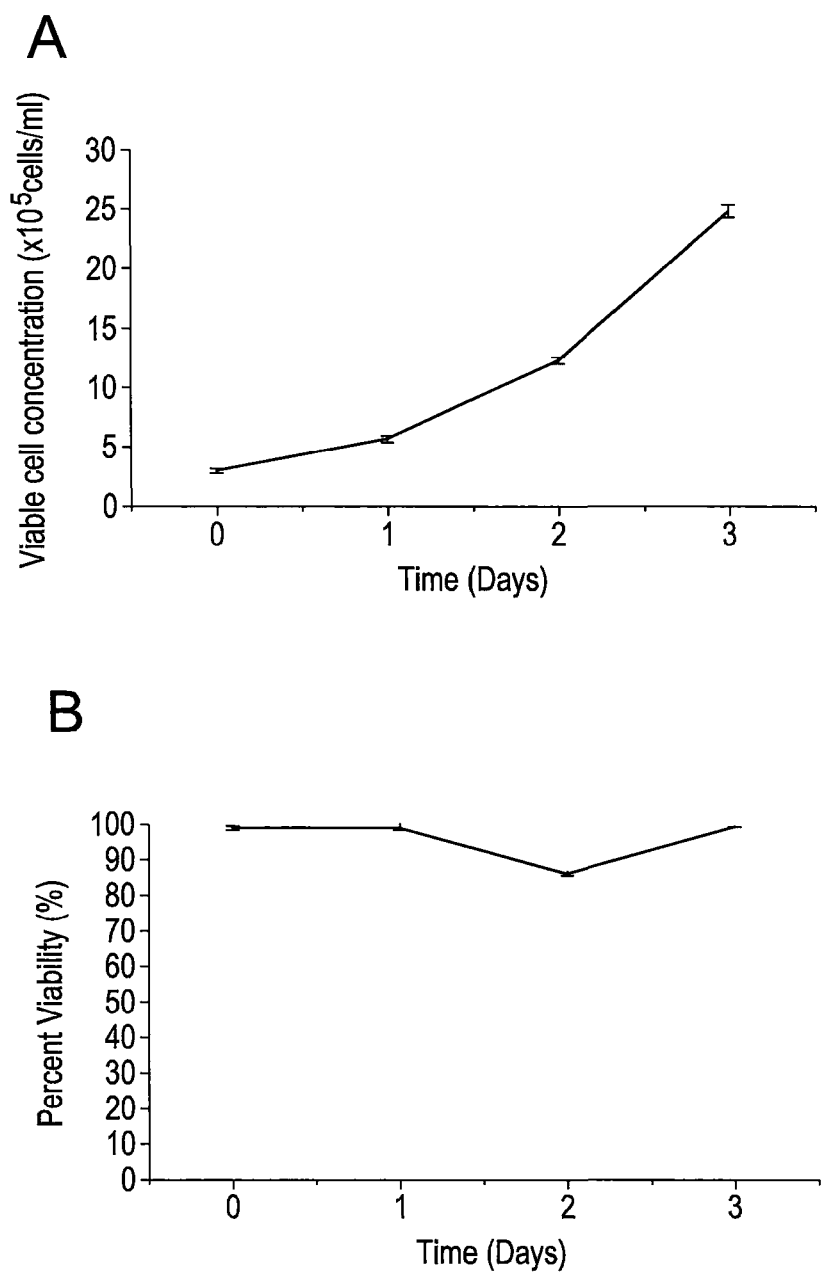

Flp-In™-CHO cells (Life Technologies) were inoculated at a density of $3 \times 10^5$ cells/ml in a total working volume of 10 ml. They were grown in CDCHO medium (Life technologies) in a 5% $CO_2$/37° C. incubator on shaking platforms operating at 140 rpm. The top of the vessel was attached to a 0.22 µm Millex GP filter (Millipore) to ensure sterility. Three day batch cultures were sampled daily and quantified by trypan blue staining (FIG. 9). For the full sequence experiments (FIG. 11(a)) cells were gown for 24 hours before being further processed.

Example 2

Centrifugation and Resuspension of Concertina Device

For all centrifugation steps the concertinas were spun in a centrifuge bucket at 1000 rpm for 5 minutes. The supernatant was removed simply by inverting and compressing the concertina. The supernatant was squeezed out of the vessel leaving the cell pellet and typically 200-300 µl of residual liquid. For resuspension the concertina was returned to an upright position before adding 10 ml of fresh medium (or in some cases cryoprotectant). The cell pellet was dislodged and a single cell suspension obtained using a standard vortex bench mixer. Cells were analysed for cell number and viability prior to centrifugation, upon resuspension and in the removed supernatant (FIG. 10)

Example 3

Cryopreservation

Figure 11:
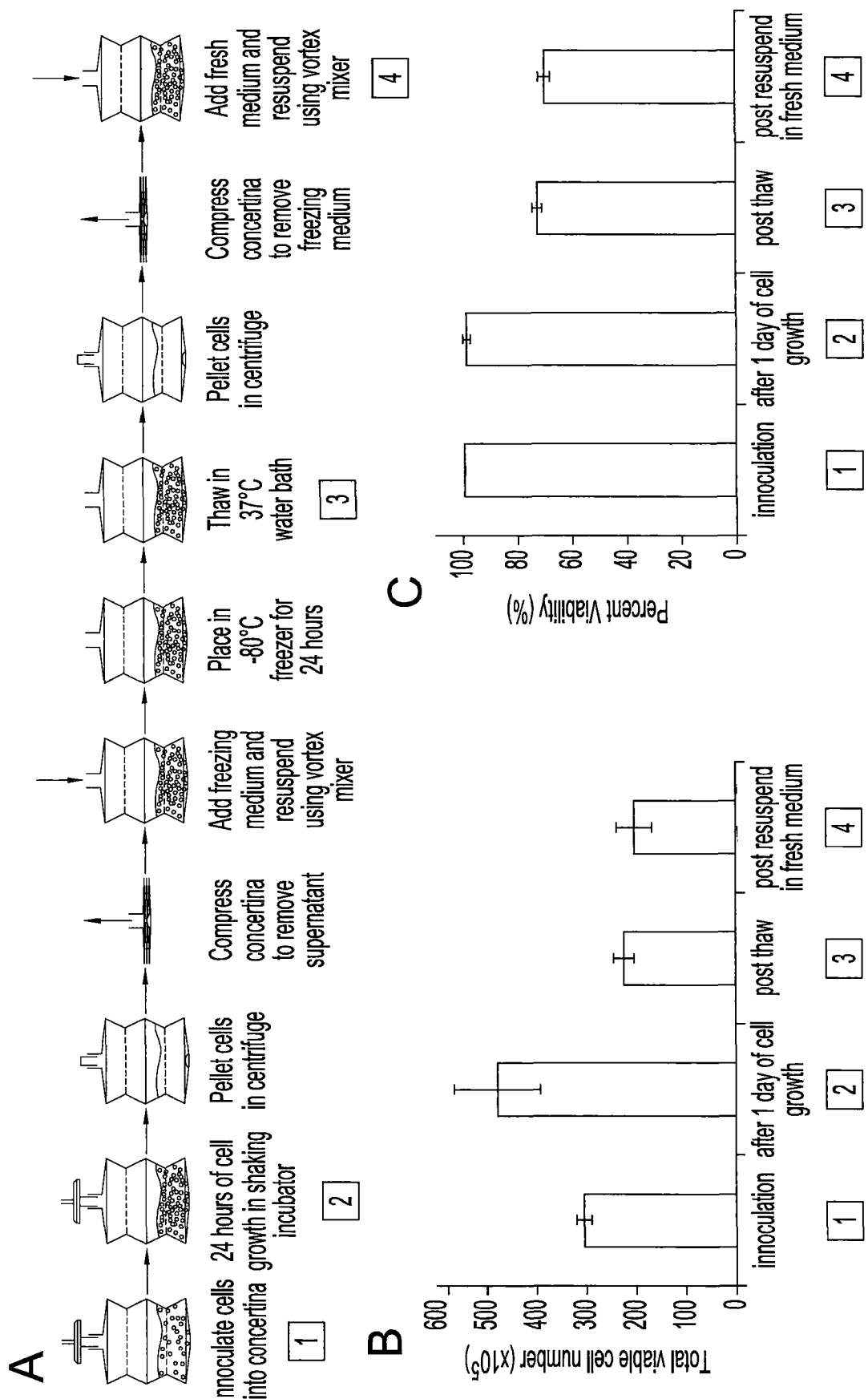

Cells were resuspended in their normal growth media supplemented with 10% (v/v) DMSO (Sigma, Poole, UK). The device was place directly into a −80° C. freezer for 24 hours before being thawed in a water bath at 37° C. The cryoprotectant was removed by centrifuging the concertina as outlined above before resuspending the cells in fresh medium. Cell counts were taken pre and post centrifugation (FIG. 11).

Example 4

Cell Counting

Viable cell concentration and viability were assessed by cell counting in an improved Neubauer haemocytometer under phase contrast microscopy. 100 μl of cells were diluted 1:1 with 0.4% (w/v) trypan blue in water (Sigma, Poole, UK). Cells from 4 grids per slide were counted and the cell death calculated based on a single grid volume of $10^{-4}$ ml. Trypan blue exclusion was also used to distinguish cells on the basis of membrane integrity. Therefore, cells that excluded trypan blue were scored as viable and those that did not were scored dead. Viability was expressed as the viable cells as a percentage of the total cell population.

Results

FIG. 9 shows the growth of CHO cells in the collapsible concertinas for three days. The growth curve is typical for these types of cells exhibiting a short lag phase before entering an exponential phase of growth after day 2 (FIG. 9(a)). On day 3 the viable cell concentration reached 24.8× $10^5$ cells/ml. Over the three days this represented an 8.2 fold increase in cell number, typical for these types of cells in normal shaker flasks. Throughout the batch culture viability was maintained above 85% indicating that the system was not inducing significant levels of cell death (FIG. 9(b)).

One of the major advantages of a collapsible cell culture device is the ability to wash cells and culture them in the same vessel. In order to demonstrate this ability a suspension of cells was centrifuged in the concertina housing under standard conditions used with traditional centrifuge tubes (1000 rpm for 5 minutes). Upon inspection a compact pellet had formed at the centre of the base of the concertina. It was found that the best method for removing the supernatant was to invert the vessel and squeeze the concertina until it was full compressed expelling the liquid into a waste container below. After this operation the cells could easily be resuspended by adding fresh medium and vortexing using a vortex bench mixer. As shown in FIG. 10 the process was highly efficient.

Prior to inoculation there was a total of 673×$10^5$ after centrifugation and resuspension we recovered 670×$10^5$ cells and there was no statistically significant difference between the two. These results show that this collapsible device is very efficient for cell washing. There was an initial concern that cells would remain within the ridges but this was not the case. Viability remained above 99% indicating that the ridges were not inducing cell death during the centrifugation process.

Finally, it was demonstrated that the device of the invention can be used all of the steps used in traditional cell culture in sequence (FIG. 11(a)). As before cells grew as expected and after 1 day of cell growth there was a 57% increase in cell number with viabilities in the high 90s (FIGS. 11(b) and 11(c)). The cells were resuspended in cryopreservation medium using the centrifugation method described above and place directly a −80° C. freezer. After 24 hours the cells were thawed and counted revealing a 53% drop in viable cell number. Viability also dropped to 69%. These losses were to be expected by the uncontrolled freezing technique. Controlled rate freezing will be essential for maintaining viability during the cryopreservation of mammalian cells and we envisage that such a system could be applied to collapsible vessels resulting in much higher viable cell numbers and viabilities. Importantly there were no further drops in viable cell number or viability upon resuspension of the cells in fresh medium indicating that the washing process could be applied to both fresh and recently thawed cells.

CONCLUSIONS

This container was successfully used for a whole chain of process operations in sequence without the cells ever leaving a single container. Cells grew as predicted when applied as a shaker flask and the same device proved effective for the centrifugation and resuspension of cells. There was some cell death observed during the cryopreservation step although this can be attributed to the lack of temperature control during the freeze step. These experiments demonstrate that a single device can be used for all of the steps involved in the culture and preservation of mammalian cells.

The invention claimed is:

1. A method of culturing cells in a cell culture container having a base section, a top section arranged in parallel with the base section and a wall element arranged between the top section and the base section and defining an internal lumen of the container, in which the wall element of the container is compressible with respect to the top and bottom section, and in which the top section of the container has an optionally sealable inlet, in which the container is composed of a flexible material, comprising culturing cells in a culture medium in the cell culture container, the method further comprising the steps of:
    (i) genetic modification; and
    (ii) cytokine stimulation; and
    (iii) expansion; and
    (iv) washing;
    wherein each step of the method is carried out within the internal lumen of the container without the cells leaving the internal lumen of the container.

2. A method of culturing cells as claimed in claim 1, in which the cell culture container is provided with an actuator means.

3. A method of culturing cells as claimed in claim 1, in which the wall section of the cell culture container comprises a plurality of lateral rigid sections in the wall arranged in parallel with the base section where each pair of lateral rigid sections is interleaved with a deformable region.

4. A method of culturing cells as claimed in claim 1, in which the wall element of the cell culture container comprises a rigid helical coil region having a deformable region provided either side of the helical coil region.

5. A method of culturing cells as claimed in claim 1, in which the lumen of the container comprises a plurality of connected chambers wherein each chamber is composed of a series of segments formed from pairs of lateral rigid sections.

6. A method of culturing cells as claimed in claim 5, in which each of the plurality of connected chambers is provided with a releasable closure means at either end of each the plurality of connected chambers.

7. A method of culturing cells as claimed in claim 1, in which a membrane or filter is located within the lumen at the deformable region to at least semi-partition the lumen into a plurality of segments formed from pairs of lateral rigid sections.

8. A method of culturing cells as claimed in claim 7, in which the membrane or filter is perforated by one or more holes.

9. A method of culturing cells as claimed in claim 7, in which the membrane or filter semi-partitions the lumen.

10. A method of culturing cells as claimed in claim 7, in which the membrane is non-contiguous with the wall element.

11. A method of culturing cells as claimed in claim 1, in which the lumen of the container has a plurality of internal wall elements arranged concentrically within the lumen of the chamber.

12. A method of culturing cells as claimed in claim 1, in which the flexible material is a gas permeable material.

13. A method of culturing cells as claimed in claim 1, in which the flexible material is selected from the group consisting of a polyethylene (optionally a low-density polyethylene (LDPE)), cis-1,4-polybutadiene, a methacrylate such as poly (ethyl methacrylate), a phthalate such as poly (ethylene terephthalate), poly (vinylidiene chloride), a cellulose such as cellulose acetate butyrate, a silicone, flouro-ethylenepolypropylene, polyolefin, or ethylene vinyl acetate copolymer.

14. A method of culturing cells as claimed in claim 1, in which container is of circular, square, rectangular, elliptical, or triangular cross section.

15. A method for culturing cells as claimed in claim 1, wherein the method further comprises one or more steps of:
   (v) cell selection; and/or
   (vi) separating; and/or
   (vii) cryopreserving the cells.

* * * * *

UNITED STATES PATENT AND TRADEMARK OFFICE
CERTIFICATE OF CORRECTION

PATENT NO. : 11,208,626 B2  
APPLICATION NO. : 15/575105  
DATED : December 28, 2021  
INVENTOR(S) : Mason et al.

Page 1 of 1

It is certified that error appears in the above-identified patent and that said Letters Patent is hereby corrected as shown below:

On the Title Page

Item (71) Applicant: "Ori Biotech Ltd." is corrected to read --Oribiotech Ltd.--

Item (73) Assignee: "Ori Biotech Ltd." is corrected to read --Oribiotech Ltd.--

Signed and Sealed this
Twenty-fourth Day of May, 2022

Katherine Kelly Vidal
*Director of the United States Patent and Trademark Office*